United States Patent [19]

Herold et al.

[11] Patent Number: 4,479,781

[45] Date of Patent: Oct. 30, 1984

[54] DISPENSER FOR METERING DENTAL COMPOSITIONS

[75] Inventors: Wolf-Dietrich Herold, Hechendorf; Rainer Grimm-Lenz, Seefeld; Bernd Burger, Hechendorf, all of Fed. Rep. of Germany

[73] Assignee: ESPE Fabrik pharmazeutischer Präparate GmbH, Seefeld, Fed. Rep. of Germany

[21] Appl. No.: 478,035

[22] Filed: Mar. 23, 1983

[30] Foreign Application Priority Data

Apr. 1, 1982 [DE] Fed. Rep. of Germany ....... 3212187

[51] Int. Cl.³ ............................................. A61C 5/04
[52] U.S. Cl. ..................................... 433/90; 222/390; 604/224
[58] Field of Search ............................ 433/90, 89, 81; 604/224, 227, 233; 222/390, 191, 470

[56] References Cited

U.S. PATENT DOCUMENTS

| 642,640 | 2/1900 | Smith | 222/390 |
| 795,270 | 7/1905 | Damon | 433/90 |
| 1,027,216 | 5/1912 | Sapp | 604/224 |
| 1,418,263 | 5/1922 | Kennedy | 222/390 |
| 2,421,711 | 6/1947 | Moots et al. | 222/390 |
| 2,573,547 | 10/1951 | Crowell | 433/90 |
| 2,859,751 | 11/1958 | Stroop | 604/227 |
| 3,993,064 | 11/1976 | McCarthy et al. | 604/224 |

FOREIGN PATENT DOCUMENTS

| 2741185 | 10/1979 | Fed. Rep. of Germany | 433/90 |
| 518022 | 2/1940 | United Kingdom | 222/390 |

Primary Examiner—John J. Wilson
Attorney, Agent, or Firm—Barnes & Thornburg

[57] ABSTRACT

A one-hand operated dispenser for metering dental compositions comprises a casing for receiving the dental composition between a forward dispensing end and a plunger which is movably mounted within the casing. The plunger is moved forwardly by means of a threaded spindle which engages with a nut disposed on the rear casing end so as to be secured against rotation and axial movement. The thus formed assembly may be inserted into two bifurcated brackets of a generally U-shaped receptacle forming part of a manipulating member. The spindle is guided in the one bracket so as to be axially movable and non-rotatable, while the casing with the nut is mounted in the other bracket so as to be non-displaceable but rotatable. When the manipulating member is gripped, the casing may be turned between thumb and index finger such that the spindle is pushed forwards, whereby the dental composition exits from the dispensing opening.

16 Claims, 2 Drawing Figures

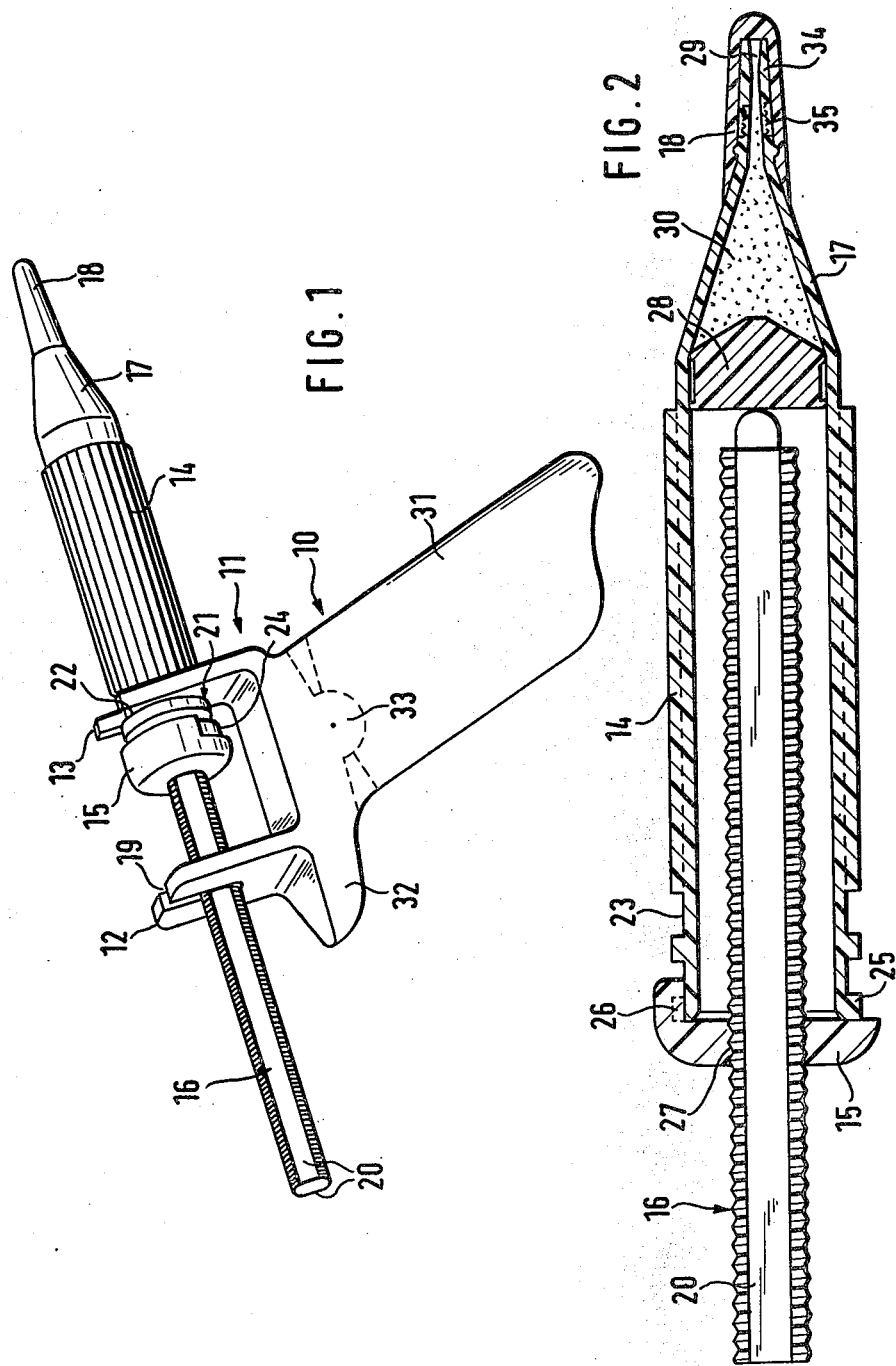

DISPENSER FOR METERING DENTAL COMPOSITIONS

DESCRIPTION

This invention relates to a one-hand operated dispenser for metering dental compsitions.

In dental practice, when dental prosthetic parts are made in laboratory and during the preservative treatment in situ, plastics compositions are used among other materials, which are initially paste-like and moldable and are subsequently cured by photopolymerization in their final molded shape.

Normally, such compositions are supplied by the manufacturer in tins out of which they are applied by means of a spatula or brush. In order to prevent premature photopolymerization it is necessary to seal the stock tins immediately upon each removal of material to protect the compositions against incident light. Experience has shown, however, that normally this is not done, especially in a dental laboratory when larger dental prosthetic parts are processed, because it would mean that the application tool has to be put down time and again, thus resulting in an increase of labor.

Furthermore, work in normally done with several differently colored compositions so as to achieve the shade of the natural teeth as accurately as possible. When, as is usual, quantities of the different compositions are successively taken out with the same application tool, an undesirable mutual carryover and mixing of the differently colored compositions will occur. In addition to the surface polymerization discussed above, which is unavoidable in actual practice, this color contamination also has the effect that the compositions will prematurely become useless.

It is an object of the invention to provide a device that can be made of few and inexpensive parts and is easily manipulated and with which dental compositions, in particular photopolymerizable compositions, may be dispensed with one hand in accurately metered quantities and applied direct onto the location that is to be processed.

In view of this object, the dispenser for metering dental compositions according to the present invention comprises (a) a casing with a dispensing opening,
(b) a plunger movable within the casing, the space defined between the plunger and the dispensing opening serving to accomodate the dental composition,
(c) a threaded spindle which acts on the plunger and is axially movable relative to the casing,
(d) a nut joined to the casing and being rotatable relative to the spindle for advancing the same, the casing, plunger, spindle and nut forming an assembly, and
(e) a manipulating member formed as a separate part and including means for receiving the assembly such that the spindle is supported non-rotatably but axially movable relative to the manipulating member and the nut is secured against axial movement relative to the manipulating member.

The dental composition is thus accomodated in a portion of a casing which is located between a plunger and a dispensing opening, and the plunger is adapted to be moved by means of a threaded spindle which is in engagement with a rotatable nut. The thus formed assembly is adapted to be inserted into the receptacle of a manipulating member which is so designed that the spindle is retained to be non-rotatable but axially movable, while the nut is retained to be rotatable and non-displaceable relative to the manipulating member.

In this structure according to the invention the dental composition is exposed only at the exit opening of the casing, which has a correspondingly small diameter already for reasons of fine metering and selective dispensing onto small surfaces to be processed. Thus, photopolymerization may occur at most on the small surface exposed within the dispensing opening. Moreover, in thin layers photopolymerization is inhibited due to the presence of oxygen, so that the composition at the dispensing opening will not be significantly cured and will in any case remain easily displaceable and dispensable.

The structure according to the invention permits simple one-hand manipulation of the device due to the fact that the entire device need merely be gripped at the manipulating member, and nothing but a turning of the nut relative to the manipulating member is required, wherein the relative positions of the member and nut during operation will not change.

The separate design of the manipulating member and the assembly formed by casing, plunger, spindle and nut renders it possible, when the respective composition has been used up, to discard said entire assembly, which consists only of a few simple parts, and to insert a freshly filled assembly into the manipulating member. Furthermore, the separate design is advantageous because normally a large number (e.g. 50) of dental compositions of different shades are kept in readiness out of which the dentist or dental technician requires only a few (typically three) for each work, so that only a correspondingly small number of manipulating members has to be available into which the respectively required container assemblies are inserted.

By the use of the device according to the invention a carryover and mutual contamination of a plurality of compositions, which occurs by means of the brush when the usual tins are employed, can be avoided.

Although German Patent Specification No. 2,741,185 discloses a device of the species mentioned above, this device is intended for other kinds of dental compositions, in particular amalgam. Due to the large number of different parts required, this prior art device is not only much more expensive to manufacture but the manipulation thereof is also rather inconvenient. For one-hand operation it is necessary that a handle mounted directly at the rear end of the spindle and also the casing itself are held stationary, and at the same time a nut has to be rotated which is provided between the handle and the casing and is supported at the rear casing end. Actually, for performing the rotating movement only the thumb is available, which can only operate by exerting pressure and therefore has a tendency of laterally displacing the device, whereby the dispensing opening may possibly be moved away from the processing location. During this operation the distance between the hand and the dispensing opening changes continually, so that the operator has to observe the position of the dispensing opening and cannot fully concentrate on the work to be done.

Moreover, during the dispensing operation the distance between the handle, which rests on the ball of the thumb, and the casing, which is held between index and middle finger, changes continually, and in consequence thereof the overall stroke of the plunger is limited to the distance between those two extreme positions of the hand between which guiding and manipulating of the device is actually possible with relative ease. At the same time, the necessary continuous change of the position of the hand will result in a substantial pressure being applied to the spindle, which in view of the rather coarse thread may result in an advance of the plunger although the nut is not intentionally rotated.

In preferred embodiments of the invention, the manipulating member includes a handle which is inclined relative to the axial direction of the assembly formed by the casing, spindle, plunger and nut and may additionally include a joint for varying the angle formed between the receptacle and the handle. A physiologically particular convenient shaping is thus obtained, and the device may be adapted to the hand of the user.

In a further embodiment, the receptacle is substantially U-shaped and includes two brackets, one of which has a slot with parallel sides for engaging lateral flattened portions of the spindle, whereas the other bracket has a substantially circular opening for rotatably supporting the nut, an outwardly open portion being provided on the circular opening which extends substantially parallel to the slot. As a result, the assembly formed by the casing, spindle, plunger and nut may be easily replaced.

A simple snap-engagement is achieved if, in a further embodiment, the open portion leaves a circular arc section of more than 180° of the circular opening and if the circular opening and the open portion are defined by resilient arms.

In another advantageous embodiment, the nut is fixed to the casing in both the axial direction and the direction of rotation, and the nut is retained relative to the receiving means by direct engagement of the casing in the receiving means. Thus, the entire axial length of the casing is available for creating the rotation. In this connection, it is preferable for the nut to be fixed to the casing by a movement transverse to the axial direction, thereby achieving a particularly simple connection between the nut and casing, fixed against rotation and axial displacement.

In a further embodiment of the invention, the nut and spindle are provided with left-hand threads. This has turned out especially favourable when the device is to be manipulated by the user's right hand.

In a still further embodiment, the casing includes a funnel-like nozzle defining the dispensing opening, the minimum inner diameter of the nozzle in the area of the dispensing opening being smaller than about 1.0 mm and preferable between 0.3 and 0.8 mm. This ensures an unobstructed view towards the location of treatment. At the same time, a minimum surface of the composition contained in the casing is exposed to light when the device is put down.

For direct in-situ application of the composition, it is particularly advantageous to provide the nozzle with an exchangeable front portion.

Preferred embodiments of the invention will be explained in detail with reference to the drawing, in which:

FIG. 1 is a perspective view of the device, and

FIG. 2 is a longitudinal sectional view through the assembly formed of casing, nut, spindle and plunger.

The dispensing device shown in FIG. 1 comprises a manipulating member 10 with a generally U-shaped receptacle 11 the two brackets 12 and 13 of which are bifuracted. An assembly formed of a generally cylindrical casing 14, a nut 15 and a threaded spindle 16 is inserted into the receptacle 11. The tip of the casing 14 is in the form of a funnel-shaped nozzle 17 the dispensing opening of which may be closed by a cap 18. The casing 14 is provided with longitudinally extending corrugations over the major part of its length.

The bracket 12 of the receptacle 11 is formed with a slot 19 having parallel sides which engage oppositely disposed flattened portions 20 of the spindle 16 such that the spindle 16 is freely movable in axial direction while being secured against rotation.

On the other hand, the bracket 13 of the receptacle 11 is formed with a circular opening 21 which is open towards the outside due to a broken-away portion 22. The opening 21 is in engagement with an annular groove 23 (see FIG. 2) formed in the rear part of the outer casing wall and supports the casing 14 with the nut 15 such that these parts are rotatable, while they cannot be moved in longitudinal direction. The nut 15 is formed with a lateral recess 24 and is fitted in lateral direction over a flange 25 (see FIG. 2) provided at the rear end of the casing and is thereby axially fixedly mounted on the casing 14. An internal protrusion 26 (see FIG. 2) projecting into a notch of the flange 25 furthermore provides for a non-rotatable connection between the nut 15 and the casing 14. A lateral slipping of the nut 15 off the casing 14 is prevented in the assembled condition by the spindle 16, which passes through a central threaded bore 27 formed in the end face of the nut 15.

Of the opening 21 in the bracket 13, the broken-away portion 22 leaves an arcuate section extending over slightly more than 180°. Furthermore, the two fork-like arms of the bracket 13 formed by the opening 21 and the broken-away portion 22 are resilient in such a manner as to permit lateral insertion of the casing 14 with the nut 15 by snap-engagement about the annular groove 23, whereby an automatic loosening of the casing 14 from the member 10 is prevented. During this lateral insertion step the spindle 16 will be placed in the slot 19. For greater ease of insertion both the slot 19 and the broken-away portion 22 are provided with external bevels.

As will be apparent from FIG. 2, the forward end of the spindle 16 is in engagement with a plunger 28 movable within the casing 14. The photopolymerizable composition which is to be dispensed is contained between the plunger 28 and the dispensing opening 29 closed by the cap 18. FIG. 2 shows the plunger 28 in its fully advanced position. In this position the casing has been emptied as far as possible and may be discarded, and a freshly filled casing may be inserted into the member 10 shown in FIG. 1. Basically, it is possible to remove the nut 15 and the spindle 16 from the emptied casing and to reuse them, as these parts will at no time contact the composition 30. But since the nut 15 and the spindle 16 as well as the casing 14, the plunger 28 and the cap 18 can be made of inexpensive plastics materials, it would appear to be more economic to discard the entire assembly shown in FIG. 2 when the available composition has been dispensed. In order to minimize the amount of composition 30 remaining inside the nozzle 17, the front face of the plunger 28 is of conical configuration, the approach angle being limited by the requirement that upon forward movement of the plunger the composition cannot penetrate behind the same.

When the device is used with the described photopolymerizable compositions, the casing 14, the nut 15 and the cap 18 are made of opaque material. Furthermore, the minimum diameter of the dispensing opening 29, which is slightly behind the forward end of the nozzle 17, is selected to be as small as possible. Typically, it is less than about 1.0 mm, preferably between 0.3 and 0.8 mm. A dispensing opening 29 which is as narrow as possible is advantageous not only from the viewpoint of dispensing very finely metered quantities, but also from the viewpoint of achieving a minimized surface of the composition 30 which is exposed upon removal of the cap 18, thereby to avoid a premature curing of the composition.

For use, the device shown in FIG. 1 is gripped by the right hand such that a handle 31 of the member 10 engages the ball of the thumb and is enclosed, for instance, by the middle, fourth and little fingers. The extension 32 will then rest in the bend between thumb and index finger. Thus the device rests securely in the hand, and at least the thumb and index finger will remain freely movable. When the casing 14 is rotated by thumb and index finger via the corrugations, the spindle 16, which is secured against rotation, will be moved and will push the plunger 28 forwardly within the casing 14, so that the composition 30 will exit from the dispensing opening 29.

Since it is easier with regard to the described position of the hand to rotate the casing 14 by an upward movement of the thumb and a downward movement of the other finger(s), both the nut 15 and the lead screw 16 are provided with a lefthand thread so as to generate a forward movement of the threaded spindle 16 for this sense of rotation of the casing 14 and nut 15.

As shown in FIG. 1, the handle 31 extends at an angle relative to the axial direction defined by the casing 14, the nut 15 and the spindle 16. An angle that is favourable for manipulating purposes is e.g. an angle of about 70°. In order to permit matching to different hand sizes and positions, it is also possible to provide a joint 33 (indicated in broken lines in FIG. 1) between the handle 31 and the receptacle 11.

As assumed above, the nozzle 17 may be integrally formed with the casing 14. In another modification indicated in FIG. 2 in broken lines, the tip 34 of the nozzle 17 may be provided at the rear end thereof with a threaded portion 35 which engages with a correspondingly threaded counter portion provided on the front part of the nozzle 17. Such an interchangeability of the nozzle tip 34 will be expedient when the device is used in dental practice for dispensing the composition in situ in the patients' mouths.

A dispenser has been described above which is intended particularly for dental compositions. The same device may also be used for metering other compositions.

We claim:

1. A dispenser for metering dental compositions, comprising
    (a) a casing with a dispensing opening,
    (b) a plunger movable within said casing, the space defined between the plunger and said dispensing opening serving to accomodate the dental composition,
    (c) a threaded spindle which acts on said plunger and is axially movable relative to said casing,
    (d) a nut fixed to said casing and engaging said spindle, said casing and nut being rotatable relative to said spindle for advancing the same, said casing, plunger, spindle and nut forming an assembly, and
    (e) a manipulating member formed as a separate part and including means removably receiving said assembly such that said spindle is supported non-rotatably but axially movable relative to the manipulating member and said casing is secured against axial movement but supported rotatably relative to the manipulating member.

2. The device of claim 1, wherein said manipulating member includes a handle which is inclined at an angle relative to the axial direction of said assembly.

3. The device of claim 2, wherein said manipulating member includes a joint for varying the angle formed between said receiving means and said handle.

4. The device of claim 1, wherein said nut and spindle are provided with lefthand threads.

5. The device of claim 1, wherein said casing includes a funnel-like nozzle defining said dispensing opening, the minimum inner diameter of the nozzle in the area of the dispensing opening being smaller than about 1.0 mm, preferably between 0.3 and 0.8 mm.

6. The device of claim 5, wherein a front portion of said nozzle is exchangeable.

7. The device of claim 1, wherein said nut is adapted to be fixed to said casing by movement transverse of said axial direction.

8. A dispenser for metering dental compositions, comprising
    (a) a casing with a dispensing opening,
    (b) a plunger movable within said casing, the space defined between the plunger and said dispensing opening serving to accommodate the dental composition,
    (c) a threaded spindle which acts on said plunger and is axially movable relative to said casing,
    (d) a nut joined to said casing and being rotatable relative to said spindle for advancing the same, said casing, plunger, spindle and nut forming an assembly, and
    (e) a manipulating member formed as a separate part and including means removably receiving said assembly such that said spindle is supported non-rotatably but axially movable relative to the manipulating member and said nut is secured against axial movement relative to the manipulating member,
    wherein said receiving means is substantially U-shaped including two brackets, one of said brackets having a first opening for axially guiding said spindle by engaging lateral flattened portions thereof, and the other bracket having a second opening for rotatably supporting said nut.

9. The device of claim 8, wherein said first opening is a slot having parallel sides for engaging said lateral flattened portions of said spindle, and said second opening is substantially circular and has an outwardly open portion parallel to said slot.

10. The device of claim 9, wherein said open portion leaves a circular arc section of more than 180° of said second opening, said second opening and said open portion being defined by resilient arms forming said other bracket.

11. The device of claim 8, wherein said nut is fixed to said casing in the axial direction and in the direction of rotation, said nut being retained relative to said receiving means by direct engagement of said casing in said receiving means.

12. The device of claim 11, wherein said nut is adapted to be fixed to said casing by a movement transverse of said axial direction.

13. A dispenser device for metering flowable compositions comprising
  (a) a casing with a dispensing opening,
  (b) a plunger movable within said casing, the space defined between the plunger and said dispensing opening serving to accomodate the composition,
  (c) a threaded spindle which acts on said plunger and is axially movable relative to said casing,
  (d) a nut joined to said casing and being rotatable relative to said spindle for advancing the same, said casing, plunger, spindle and nut forming an assembly, and
  (e) a manipulating member formed as a separate part and including receiving means receiving said assembly such that said spindle is supported non-rotatably but axially movable relative to the manipulating member and said nut is secured against axial movement relative to the manipulating member,
  wherein said receiving means includes a first bracket means having a first opening for axially guiding said spindle and a second bracket means having a second opening for rotatably supporting said nut.

14. A dispenser device according to claim 13, wherein said spindle has at least one flattened section extending in its axial direction, and wherein wall portions of said first opening slidably engage said flattened section when in an in-use position.

15. A dispenser device according to claim 14, wherein said spindle includes two flattened sections at opposite lateral sides of the spindle, and wherein said first opening includes lateral sidewall portions slidably engagable with the respective flattened sections when in an in-use position.

16. A dispenser device for measuring flowable compositions comprising
  (a) a casing with a dispensing opening,
  (b) a plunger movable within said casing, the space defined between the plunger and said dispensing opening serving to accomodate the composition,
  (c) a threaded spindle which acts on said plunger and is axially movable relative to said casing
  (d) a nut fixed to said casing and engaging said spindle, said casing and nut being rotatable relative to said spindle for advancing the same, said casing, plunger, spindle and nut forming an assembly, and
  (e) a manually operable manipulating member formed as a separate part and including receiving means removably receiving said assembly such that said spindle is supported non-rotatably but axially movable relative to the manipulating member and said casing is secured against axial movement but supported rotatably relative to the manipulating member,
  wherein said receiving means includes first guide means for slidably engaging said spindle to axially guide said spindle and second guide means for rotatably supporting the nut, said first and second guide means being axially spaced from one another along the length of the spindle when in an in-use position.

* * * * *